United States Patent
Toba et al.

(10) Patent No.: US 6,929,806 B2
(45) Date of Patent: Aug. 16, 2005

(54) AGENTS FOR IMPROVING LIPID METABOLISM AND REDUCING HIGH BLOOD PRESSURE

(75) Inventors: Yasuhiro Toba, Musashino (JP);
Yukihiro Takada, Kawagoe (JP);
Yoshikazu Morita, Kawagoe (JP);
Takumi Abe, Kawagoe (JP); Hiroshi Kawakami, Kawagoe (JP)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 0 days.

(21) Appl. No.: 10/789,193

(22) Filed: Feb. 27, 2004

(65) Prior Publication Data

US 2004/0167078 A1 Aug. 26, 2004

Related U.S. Application Data

(62) Division of application No. 10/050,459, filed on Jan. 15, 2002, now abandoned.

(30) Foreign Application Priority Data

Jan. 16, 2001 (JP) ............................................ 2001-8189
Jan. 16, 2001 (JP) ............................................ 2001-8190

(51) Int. Cl.$^7$ .............................................. A61K 35/20
(52) U.S. Cl. .............................. 424/535; 514/2; 514/21
(58) Field of Search .............................. 424/535; 514/2, 514/21

(56) References Cited

U.S. PATENT DOCUMENTS 5,866,418 A * 2/1999 Ballard et al. .............. 435/384
6,183,784 B1 * 2/2001 Read et al. .................. 424/535

FOREIGN PATENT DOCUMENTS

EP 0 786 473 A2 7/1997

OTHER PUBLICATIONS

Steve L. Taylor, "Handbook of Milk Composition," Academic Press Inc. p. 467 1995.

Anne Pihlanto, et al., "Angiotensin 1–converting enzyme inhibitory properties of whey protein digests: concentration and characterization of active peptides," Journal of Dairy Research (2000) 67 pp. 53–64.

Amhar Abubakar, et al., "Structural Analysis of New Anti-hypertensive Peptides Derived from Cheese Whey Protein by Proteinase K Digestion," J. Dairy Sci 81 pp. 3131–3138 1998.

Masafumi Maeno, "Identification of an Antihypertensive Peptide from Casein Hydrolysate Produced by a Proteinase from *Lactobacillus helveticus* CP790," J Dairy Sci 79 pp. 1316–1321 1996.

Naoyuki Yamamoto, et al., "Antihypertensive Effect of the Peptides Derived from Casein by an Extracellular Proteinase from *Lactobacillus helveticas* CP790," J Dairy Sci 77 pp. 917–922 1994.

* cited by examiner

*Primary Examiner*—Jean C. Witz
(74) *Attorney, Agent, or Firm*—Knobbe, Martens, Olson & Bear LLP

(57) ABSTRACT

A milk-derived basic protein fraction and a basic peptide fraction are provided for use as an effective component for agents for improving lipid metabolism and reducing high blood pressure which can be administered orally, are effective with a relatively small dosage, have good taste and are stable during storage.

4 Claims, No Drawings

AGENTS FOR IMPROVING LIPID METABOLISM AND REDUCING HIGH BLOOD PRESSURE

This is a divisional of U.S. application Ser. No. 10/050,459 filed Jan. 15, 2002, now abandoned, which claims priority based on Japanese Patent Application Nos. 2001-8189 and 2001-8190 filed Jan. 16, 2001, and the complete disclosure of which is hereby incorporated by this reference thereto.

BACKGROUND OF THE INVENTION

1. Field of the Invention

The present invention relates to agents, drinks and food products for improving lipid metabolism and reducing high blood pressure and the combination thereof that are effective in treating and preventing diseases such as fatty liver, hyperlipidemia, arteriosclerosis, obesity and hypertension.

2. Description of the Related Art

Lipid metabolism refers to catabolic (decomposing) and anabolic (accumulating) in vivo processes of lipids, mainly comprising triglicerides derived from food. Lipid metabolism generally includes energy-releasing reaction of lipids, biosynthesis of fatty acids, biosynthesis of acylglycerols, phospholipid metabolism, cholesterol metabolism, and the like ("Biochemistry for Nutrition" by Akira Misaki, Asakura Shoten, 1993, pp. 123–134).

In recent years, the mortality rate from cardiovascular disease has been rapidly increasing and the correlation between the risk of getting cardiovascular disease and the blood cholesterol concentration has been pointed out. Meantime, several attempts have been made to reduce the blood cholesterol concentration by using food materials, which can be ingested in daily life. For example, soybean protein (*Arteriosclerosis* 1988 72:115), whey protein (*Agric Biol Chem* 1991 55:813; Japanese Patent Application Laid-open No. H5-176713), soybean protein hydrolyzates (*J Nutr* 1990 120:977), and egg yolk phospholipid (*Agric Biol Chem* 1989 53:2469) have been tried. Further, a method making use of lactoalbumin, collagen, soybean protein or wheat gluten and soybean lecithin in combination (*Nutr Rep Int* 1983 28:621) and a method making use of tissue-like soybean protein containing soybean lecithin (*Ann Nutr Metab* 1985 29:348), and the like have been proposed.

High blood pressure refers to essential hypertension, etiology of which is unknown, and secondary hypertension, which is associated with disease of the kidney, adrenal gland or nervous system. In recent years, 90% of cases are reported to be essential hypertension. Today, antihypertensive agents are frequently used for the prevention and treatment of essential hypertension. However, every conventional antihypertensive agent has a disadvantage to show a certain adverse effect. For example, individual drugs show characteristic adverse effects: antihypertensive diuretics cause hypokaliemia or acidemia, antihypertensive peripheral vasodilators cause hypoglobulia, β-blockers cause bronchoasthma, and α-methyldopa increases glutamic-oxaloacetic transaminase (GOT) or glutamic-pyruvic transaminase (GPT) values in the blood and causes hemolytic anemia. Accordingly, a special consideration is required in administering these antihypertensive agents, and the dosage and period of administration for these agents are naturally restricted.

Under the abovementioned circumstances, development of antihypertensive agents without adverse effects has been strongly urged, and antihypertensive agents having a microorganism-derived substance as an effective component have drawn attention. Such substances comprise, for example, high molecular weight polysaccharides derived from lactic acid bacteria as an effective component (Japanese Patent Application Laid-open No. S59-190929), glycoproteins having a molecular weight of more than 10,000 isolated from chlorella algae (Japanese Patent Application Laid-open No. S60-45603), viable or dead cells of bacteria of genus *Streptococcus* (Japanese Patent Application Laid-open S61-221124), dried beer yeast as an effective component (Japanese Patent Application Laid-open No. S63-255234), or a hot water extract of lactic acid bacteria (Japanese Patent Application Laid-open S63-139129; Japanese Patent Application Laid-open No. H2-247127). However, many of these substances are water insoluble and have unpleasant taste, which prevent them from practical use.

Therefore, attempts have been made to develop antihypertensive agents comprising substances contained in food materials, which can be administered orally in daily life, as an effective component. For example, an enzyme-digested casein product (*Food Develop* 1997 32:37–39), and an enzyme-digested fish meat product (*Health Nutr Food Res* 1998 1:62–71; *Food Develop* 1996 31:50–52) have been reported.

However, the methods described above have problems such that a relatively large amount of ingestion is required, that flavor is not desirable, and that precipitation occurs during storage when made into drinks interfering with stable storage.

More importantly, no substance which can improves lipid metabolism and reduce high blood pressure simultaneously is known. A problem in lipid metabolism can be a cause of raising blood pressure, and in that case, inadequate lipid metabolism is associated with high blood pressure. For example, in some cases, high blood cholesterol levels tend to cause arteriosclerosis which leads to high blood pressure. Thus, if a substance which can both improve lipid metabolism and reduce high blood pressure is developed, the problem in both lipid metabolism and blood pressure can effectively be resolved.

SUMMARY OF THE INVENTION

The present inventors found that a milk-derived basic protein fraction or a basic peptide fraction, which is obtained by digesting said basic protein fraction with a protease, e.g. pepsin and pancreatin, can improve lipid metabolism and reduce high blood pressure when administered orally. Further, the inventors found that these basic protein fraction and basic peptide fraction can be effectively used as an effective component for agents and drinks or food products for improving lipid metabolism and high blood pressure and the combination thereof.

In one embodiment an agent for improving lipid metabolism is provided comprising a milk-derived basic protein fraction as an effective component and a suitable carrier (e.g., for oral administration). Preferably, this milk-derived basic protein fraction contains 15% or more by weight basic amino acids in its amino acid composition. Preferably, the milk-derived basic protein fraction is obtained by bringing milk or a milk-derived material into contact with cation exchange resins to adsorb basic proteins and eluting a fraction adsorbed on the resins with an eluent having a salt concentration of about 0.1 M to about 1.0 M.

In another embodiment an agent for improving lipid metabolism is provided comprising a basic peptide fraction as an effective component which is obtained by digesting the milk-derived basic protein fraction by a protease. Preferably, the milk-derived basic protein fraction is digested by at least one of proteases selected from the group consisting of pepsin, trypsin, chymotrypsin, and pancreatin.

In another embodiment a drink or food product for improving lipid metabolism is provided to which the milk-derived basic protein fraction or basic peptide fraction of the present invention is admixed.

In another embodiment an agent for reducing high blood pressure is provided comprising a milk-derived basic protein fraction as an effective component and a suitable carrier (e.g., for oral administration). Preferably, this milk-derived basic protein fraction contains 15% or more by weight basic amino acids in its amino acid composition. Preferably, the milk-derived basic protein fraction is obtained by bringing milk or a milk-derived material into contact with cation exchange resins to adsorb basic proteins and eluting a fraction adsorbed on the resins with an eluent having a salt concentration of about 0.1 M to about 1.0 M.

In another embodiment an agent for reducing high blood pressure is provided comprising a basic peptide fraction as an effective component which is obtained by digesting the milk-derived basic protein fraction by a protease. Preferably the milk-derived basic protein fraction is digested by at least one of proteases selected from the group consisting of pepsin, trypsin, chymotrypsin, and pancreatin.

In another embodiment a drink or food product for reducing high blood pressure is provided to which the milk-derived basic protein fraction or basic peptide fraction of the present invention is admixed.

An agent for improving lipid metabolism and an agent for reducing high blood pressure can include basically the same component. By examining activities and effects on each lipid metabolism and blood pressure with respect to the content of the component and other supplemental ingredients, desired balance therebetween can readily be achieved. Agents for improving lipid metabolism and/or reducing high blood pressure of the present invention can be administered not only to a patient having the symptoms but also to a candidate for the treatment of preventing these symptoms.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. Further aspects, features and advantages of this invention will become apparent from the detailed description of the preferred embodiments which follow.

DETAILED DESCRIPTION OF THE PREFERRED EMBODIMENT

Agents for improving lipid metabolism and reducing high blood pressure and a combination thereof are characterized in that they contain a milk-derived basic protein fraction or a basic peptide fraction as an effective component. Said milk-derived basic protein fraction can be obtained from mammalian milk such as cow milk, human milk, goat milk, and ewe milk. The basic peptide fraction can be obtained by digesting the milk-derived basic milk fraction of the present invention with a protease.

In an embodiment, this milk-derived basic protein fraction has the following characteristics as described hereinafter in Test Examples 1 through 3. The present invention is not limited to this embodiment.

1) It comprises various proteins having a molecular weight ranging from about 2,000 to about 80,000, preferably from about 3,000 to about 24,000, according to sodium dodecyl sulfate polyacrylamide gel electrophoresis (SDS-PAGE). It has an isoelectric point ranging from about 7.5 to about 11, preferably from about 8 to about 10.

2) It contains more than about 95% by weight protein and small amounts of fat and ash.

3) Proteins contained are mainly lactoferrin and lactoperoxidase.

4) As for the amino acid composition of proteins, it contains more than about 15% by weight basic amino acids such as lysine, histidine and arginine.

Such a basic protein fraction can be obtained, for example, by bringing a milk material, such as skimmed milk and whey, into contact with cation exchange resins to adsorb basic proteins, eluting a basic protein fraction adsorbed on these resins with an eluent having a salt concentration of about 0.1 M to about 1.0 M, recovering this eluate fraction, desalting and concentrating this fraction with a reverse osmotic (RO) membrane or by the electrodialysis (ED) method, and drying the resulting fraction, if necessary.

Further, a milk-derived basic protein fraction can be obtained, for example, by a method in which milk or milk-derived material is brought into contact with cation exchanger to adsorb basic proteins, and then a basic protein fraction adsorbed on this cation exchanger is eluted with an eluent having a pH higher than 5 and an ionic strength greater than 0.5 (Japanese Patent Application Laid-open No. H5-202098), a method in which alginic acid gel is used (Japanese Patent Application Laid-open No. S61-246198), a method in which the fraction is obtained from whey using inorganic porous particles (Japanese Patent Application Laid-open No. H1-86839), and a method in which the fraction is obtained from milk using a sulfate ester compound (Japanese Patent Application Laid-open No. S63-255300). In the present invention, a basic protein fraction obtained by any of such a method can be used. The disclosure of the above references is herein incorporated by reference.

Further, a milk-derived basic peptide fraction has the same amino acid composition as the basic protein fraction. For example, the milk-derived basic protein fraction obtained by any of the abovementioned methods is treated with protease such as pepsin, trypsin, and chymotrypsin, and if necessary further with protease such as pancreatin, to obtain a peptide composition having an average molecular weight of less than about 4,000, preferably from about 1,000 to about 3,000.

In administering agents of the present invention for improving lipid metabolism and reducing high blood pressure and the combination thereof, a milk-derived basic protein fraction or the basic peptide fraction as an effective component can be used without further processing. Also, the milk-derived basic protein and basic peptide fractions of the present invention can be formulated into powders, granules, tablets, capsules, drinks, or the like according to conventional methods. Further, these basic protein fraction and basic peptide fraction, without further processing or after formulation, can be admixed with nutrients, drinks or food products to improve lipid metabolism and reduce high blood pressure. An increased activity for improving lipid metabolism and reducing high blood pressure and the combination thereof can be expected by admixing the basic protein fraction or the basic peptide fraction of the present invention along with other components which are considered to have an activity to improve lipid metabolism (e.g., 50 to 50,000% by weight with respect to the basic protein fraction or the basic peptide fraction), such as soybean protein, whey protein, soybean lecithin, diacylglycerol, and soybean isoflavone, as well as the other components which are considered to have an antihypertensive activity (e.g., 100 to 50,000% by weight with respect to the basic protein fraction or the basic peptide fraction), such as calcium, magnesium, potassium, and dietary fiber. For example, 10 g of soybean protein and 40 mg of soybean isoflavone can be used with 20 to 100 mg of the milk-derived basic protein fraction. In other examples, 10 g of dietary fiber and 100 mg of magnesium can be used with 20 to 100 mg of the milk-derived basic protein fraction. By adjusting the amounts of the above supplemental components, an activity of improving lipid metabolism and an activity of lowering blood pressure can effectively be balanced. Further, materials containing the milk-derived basic protein fraction or basic peptide fraction of the present invention can be sterilized by heating under ordinary conditions known to a skilled artisan (for example, at 90° C. for 10 min., at 121° C. for 2 sec.) since the milk-derived basic protein fraction and basic peptide fraction of the present invention are relatively heat-stable.

For the purpose of this invention the "effective component" means causing a result, such as the improvement of lipid metabolism, reduction of high blood pressure, or both.

The dosage of agents for improving lipid metabolism and reducing high blood pressure and the combination thereof according to the present invention varies depending on age, therapeutic effect and pathologic conditions. However, results of animal experiments using rats revealed that an administration of 20 mg or more of a basic protein fraction or basic peptide fraction per kg body weight of rat was necessary to improve lipid metabolism and high blood pressure. Therefore, according to an extrapolation method (A Sequel to Medicinal Development, 1993 8:7–18), an effective daily dose for a human adult is estimated to be about 20 mg or more, preferably from about 20 to about 1000 mg, more preferably from about 40 to about 100 mg. Accordingly, the fractions can be admixed with drinks or food products or administered as a medicine so as to securely attain this dosage (for example, 2 m % to 2% in a drink or food product, 0.2% to 20% in a medicine).

The present invention is described in but is not limited to the following examples and test examples.

EXAMPLE 1

A column (5 cm in diameter and 30 cm in height) filled with cation exchange resins, sulfonated Chitopearl (400 g; a product of Fuji Boseki Co., Ltd.), was thoroughly washed with deionized water. Skimmed milk (40 L, pH 6.7) was passed through the column at a flow rate of 25 ml/min, after which the column was thoroughly washed with deionized water, and then a fraction of basic proteins adsorbed on the resins was eluted with a 0.02 M carbonic acid buffer solution (pH 7.0) containing 0.98 M sodium chloride. The resulting eluate was desalted and concentrated using a reverse osmotic (RO) membrane and then freeze-dried to obtain 21 g of a powdered basic protein fraction.

Test Example 1

The basic protein fraction obtained in Example 1 was subjected to sodium dodecyl sulfate polyacrylamide gel electrophoresis (SDS-PAGE), which revealed that the molecular weights of the proteins ranged from about 3,000 to about 80,000.

Test Example 2

The composition of the basic protein fraction obtained in Example 1 was analyzed. Results are shown in Table 1. As shown in Table 1, protein is the major component of this fraction.

TABLE 1

|  | Unit: % by weight |
| --- | --- |
| Water | 1.06 |
| Protein | 96.5 |
| Fat | 0.56 |
| Ash | 0.27 |
| Others | 1.61 |

Test Example 3

The amino acid composition of the basic protein fraction obtained in Example 1 was analyzed using an amino acid analyzer (Model L-8500, a product of Hitachi Ltd.) after hydrolysis with 6 N hydrochloric acid at 110° C. for 24 hours. Results are shown in Table 2. This basic protein fraction contains more than 15% by weight basic amino acids (lysine, histidine and arginine) in its amino acid composition.

TABLE 2

|  | Unit: % by weight |
| --- | --- |
| Aspartic acid | 10.1 |
| Serine | 5.3 |
| Glutamic acid | 12.3 |
| Proline | 4.7 |
| Alanine | 5.7 |
| Leucine | 10.2 |
| Lysine | 8.4 |
| Histidine | 2.5 |
| Arginine | 7.2 |
| Others | 33.6 |

EXAMPLE 2

A column (100 cm in diameter and 10 cm in height) filled with cation exchange resins, SP Toyopearl (30 kg; a product of Toso), was thoroughly washed with deionized water. Cheese whey (30 t, pH 6.2) which was sterilized by heating at 121° C. for 30 seconds was passed through the column at a flow rate of 10 L/min, after which the column was thoroughly washed with deionized water, and then a fraction of basic proteins adsorbed on the resins was eluted with a 0.1 M citric acid buffer solution (pH 5.7) containing 0.9 M sodium chloride. The resulting eluate was desalted and concentrated by an electrodialysis (ED) method and then freeze-dried to obtain 183 g of a powdered basic protein fraction.

EXAMPLE 3

The basic protein fraction powder obtained in Example 1 (50 g) was dissolved in 10 L of distilled water, 50 ml of a 1% by weight solution of pancreatin (a product of Sigma) was added, and reaction was carried out at 37° C. for 2 hours. To stop the reaction, the enzyme was inactivated by heating at 80° C. for 10 minutes, after which the reaction solution was concentrated and freeze-dried to obtain 48.3 g of a powdered basic peptide fraction.

Test Example 4

For the powdered basic protein fraction obtained in Example 1 and the powdered basic peptide fraction obtained in Example 3, an activity to improve lipid metabolism was examined by an animal experiment using Wistar male rats (4 weeks of age). The rats were divided into 5 experimental groups (N=8): a group to which physiological saline was administered (group A), a group to which 20 mg of the powdered basic protein fraction per kg body weight of rat were administered (group B), a group to which 200 mg of the powdered basic protein fraction per kg body weight of rat were administered (group C), a group to which 20 mg of the powdered basic peptide fraction per kg body weight of rat were administered (group D), a group to which 200 mg of the powdered basic peptide fraction per kg body weight of rat were administered (group E). The administration was carried out using a gavage once a day for 10 weeks. During this 10-week period, animals were fed feed containing 1% by weight cholesterol and 0.25% by weight sodium cholate.

Following the 10 weeks of administration of the powdered basic protein fraction or powered basic peptide fraction, the total cholesterol, high-density lipoprotein cholesterol, low-density and very low-density lipoprotein cholesterols, and neutral fat in the serum were measured. Results are shown in Table 3.

TABLE 3

|  | Group A | Group B | Group C | Group D | (Unit: mg/dl) Group E |
|---|---|---|---|---|---|
| Tchol | 145 ± 13$^a$ | 112 ± 15$^b$ | 90 ± 16$^{b,c}$ | 109 ± 16$^{b,c}$ | 88 ± 18$^c$ |
| HDL | 37 ± 9 | 35 ± 6 | 44 ± 10 | 37 ± 9 | 45 ± 7 |
| LDL + VLDL | 108 ± 8$^a$ | 77 ± 13$^b$ | 47 ± 10$^c$ | 72 ± 14$^b$ | 43 ± 12$^c$ |
| TG | 194 ± 19$^a$ | 173 ± 18$^a$ | 136 ± 22$^b$ | 169 ± 27$^{a,b}$ | 136 ± 32$^b$ |

TChol: total cholesterol;
HDL: high-density lipoprotein cholesterol;
LDL: low-density lipoprotein cholesterol;
VLDL: very low-density lipoprotein cholesterol;
TG: neutral fat.
Superscripts in Table 3 show significant difference between different groups ($p < 0.05$).

The results showed that in all experimental groups, i.e., group B, group C, group D and group E the total cholesterol was significantly lower compared to the control group, i.e., group A. In detail, the figures for the low-density and very low-density lipoprotein cholesterols, which are considered to be bad cholesterols, were significantly lower in group B, group C, group D, and group E as compared to group A while the figures for the high-density lipoprotein, which is considered to be good cholesterol, were not significantly different between the groups. Figures for the neutral fat were significantly lower in group C and group E as compared to group A.

These results revealed that the basic protein fraction and the basic peptide fraction have an activity to lower the levels of serum cholesterols, particularly the low-density and very low-density cholesterols, which are considered to be bad cholesterols, and the levels of serum neutral fat, thereby improving lipid metabolism.

Further, it was revealed that the activity to improve lipid metabolism was observed when at least 20 mg per kg rat body weight of the basic protein fraction or the basic peptide fraction were administered.

Test Example 5

For the powdered basic protein fraction obtained in Example 1 and the powdered basic peptide fraction obtained in Example 3, an activity to lower blood pressure was examined in vivo using SHR rats which had a congenital hypertensive genetic factor. SHR male rats (4 weeks old) were divided into 5 experimental groups (N=8): a group to which physiological saline was administered (group A), a group to which 20 mg of the powdered basic protein fraction per kg body weight of rat were administered (group B), a group to which 200 mg of the powdered basic protein fraction per kg body weight of rat were administered (group C), a group to which 20 mg of the powdered basic peptide fraction per kg body weight of rat were administered (group D), a group to which 200 mg of the powdered basic peptide fraction per kg body weight of rat were administered (group E). The administration was carried out using a gavage once a day for 8 weeks. After 4 weeks and 8 weeks, systolic blood pressure was measured. Results are shown in Table 4.

TABLE 4

|  | Group A | Group B | Group C | Group D | (Unit: mm Hg) Group E |
|---|---|---|---|---|---|
| After 4 weeks | 238 ± 15$^a$ | 226 ± 13$^{a,b}$ | 221 ± 11$^b$ | 231 ± 8$^{a,b}$ | 217 ± 13$^b$ |
| After 8 weeks | 242 ± 13$^a$ | 221 ± 9$^b$ | 212 ± 7$^b$ | 222 ± 10$^b$ | 214 ± 18$^b$ |

Superscripts in Table 4 show significant difference between different groups ($p < 0.05$).

The results showed that after 4 weeks, experimental groups, C and E showed significantly lower systolic blood pressure compared to the control group, i.e., group A. Further, the systolic blood pressure after 8 weeks was significantly lower in group B, group C, group D, and group E compared to group A.

These results revealed that the basic protein fraction and the basic peptide fraction have an antihypertensive activity.

Further, it was revealed that the antihypertensive activity was observed when at least 20 mg per kg rat body weight of the basic protein fraction or the basic peptide fraction were administered.

EXAMPLE 4

A drink for improving lipid metabolism and reducing high blood pressure having the composition shown in Table 5 was produced. The taste of the resulting drink was good and did not deteriorate during storage for one year at room temperature, without precipitation or the like.

TABLE 5

|  | (Unit: % by weight) |
|---|---|
| Mixed isomerized sugars | 15 |
| Fruit juice | 10 |
| Citric acid | 0.5 |
| Basic protein fraction powder (Example 1) | 0.1 |
| Flavoring | 0.1 |
| Mineral | 0.1 |
| Water | 74.2 |

EXAMPLE 5

Dough having the composition shown in Table 6 was prepared, molded and baked to produce biscuits for improving lipid metabolism.

TABLE 6

| | (Unit: % by weight) |
|---|---|
| Flour | 50 |
| Sugar | 20 |
| Table salt | 0.5 |
| Margarine | 12.5 |
| Egg | 11.5 |
| Water | 2.5 |
| Mineral mixture | 0.8 |
| Basic protein fraction powder (Example 2) | 1.2 |
| Soybean isoflavone | 1 |

Dough having the composition shown in Table 7 was prepared, molded and baked to produce antihypertensive biscuits.

TABLE 7

| | (Unit: % by weight) |
|---|---|
| Flour | 50 |
| Sugar | 20 |
| Table salt | 0.5 |
| Margarine | 12.5 |
| Egg | 12.5 |
| Water | 2.5 |
| Mineral mixture | 0.8 |
| Basic protein fraction powder (Example 2) | 1.2 |

EXAMPLE 6

Tablets for improving lipid metabolism having the composition shown in Table 8 were produced.

TABLE 8

| | (Unit: % by weight) |
|---|---|
| Hydrous crystalline glucose | 73.5 |
| Soybean protein | 10 |
| Basic protein fraction powder (Example 2) | 10 |
| Mineral mixture | 5 |
| Sugar esters | 1 |
| Flavoring | 0.5 |

Antihypertensive tablets having the composition shown in Table 9 were produced.

TABLE 9

| | (Unit: % by weight) |
|---|---|
| Hydrous crystalline glucose | 83.5 |
| Basic protein fraction powder (Example 2) | 10 |
| Mineral mixture | 5 |
| Sugar esters | 1 |
| Flavoring | 0.5 |

Since the agents, drinks and food products for improving lipid metabolism and reducing high blood pressure of the present invention can improve lipid metabolism and reduce high blood pressure through ingestion, they are effective in treating and preventing diseases such as fatty liver, hyperlipidemia, arteriosclerosis, obesity, and hypertension.

While the present invention has been described in some detail for purposes of clarity and understanding, one skilled in the art will appreciate that various changes in form and detail can be made without departing from the true scope of the invention. All patents, patent applications and publications referred to above are hereby incorporated by reference. Further, this application claims priority to Japanese Patent Application No. 2001-008189 and No. 2001-008190, both filed Jan. 16, 2001, and the disclosure of which is herein incorporated by reference in its entirety.

What is claimed is:

1. A method of improving lipid metabolism and/or reducing high blood pressure comprising administering an effective amount of a milk-derived basic protein fraction to a candidate for the treatment or a patient in need thereof.

2. A method of improving lipid metabolism and/or reducing high blood pressure according to claim 1, comprising orally administering about 20 mg or more of the milk-derived basic protein fraction per day.

3. A method of improving lipid metabolism and/or reducing high blood pressure comprising administering an effective amount of a basic peptide fraction which is obtained by digesting a milk-derived basic protein fraction with a protease to a candidate for the treatment or a patient in need thereof.

4. A method of improving lipid metabolism and/or reducing high blood pressure according to claim 3, comprising orally administering about 20 mg or more of the basic peptide fraction per day.

* * * * *